US008722096B2

(12) United States Patent
Boltri et al.

(10) Patent No.: US 8,722,096 B2
(45) Date of Patent: May 13, 2014

(54) LIPOIC ACID PELLETS

(75) Inventors: Luigi Boltri, Agrate Brianza (IT); Flavio Fabiani, Milan (IT); Luigi Mapelli, Milan (IT); Annibale Salvi, Milan (IT); Paolo Magri', Castel San Pietro (CH); Antonio Nardi, Paderno Dugnano (IT); Flavio Villani, Parma (IT)

(73) Assignees: Aptalis Pharma Limited, Bray (IE); Laboratorio Chimico Internazionale S.p.A., Milan (IT)

( * ) Notice: Subject to any disclaimer, the term of this patent is extended or adjusted under 35 U.S.C. 154(b) by 1130 days.

(21) Appl. No.: 12/302,260

(22) PCT Filed: May 25, 2007

(86) PCT No.: PCT/EP2007/055124
§ 371 (c)(1),
(2), (4) Date: Nov. 24, 2008

(87) PCT Pub. No.: WO2007/138022
PCT Pub. Date: Dec. 6, 2007

(65) Prior Publication Data
US 2009/0117232 A1    May 7, 2009

(30) Foreign Application Priority Data
May 25, 2006  (IT) .............................. MI2006A1024

(51) Int. Cl.
*A61K 9/16* (2006.01)
*A61K 9/50* (2006.01)
*C07D 339/04* (2006.01)

(52) U.S. Cl.
CPC ............. *A61K 9/5078* (2013.01); *A61K 9/1652* (2013.01); *C07D 339/04* (2013.01)
USPC ........................................................ 424/494

(58) Field of Classification Search
None
See application file for complete search history.

(56) References Cited

U.S. PATENT DOCUMENTS

| 5,626,875 | A  | * | 5/1997  | Ballester Rodes et al. ... 424/464 |
| 6,740,341 | B1 | * | 5/2004  | Holt et al. ..................... 424/490 |
| 2001/0028896 | A1 | * | 10/2001 | Byrd ............................. 424/457 |
| 2002/0098247 | A1 | * | 7/2002  | Komorowski et al. ........ 424/655 |
| 2005/0106247 | A1 | * | 5/2005  | Venkatesh et al. ............ 424/469 |
| 2005/0256178 | A1 | * | 11/2005 | Eggersdorfer et al. ....... 514/393 |
| 2006/0280843 | A1 | * | 12/2006 | Jager et al. .................... 426/112 |

FOREIGN PATENT DOCUMENTS

| JP | 63-192725 A  | 8/1988 |
| JP | 2002-516270 A | 6/2002 |
| WO | 9961004 A1   | 12/1999 |
| WO | 2005046561 A2 | 5/2005 |

OTHER PUBLICATIONS

Wikipedia "dietary supplement" (http://en.wikipedia.org/wiki/Dietary_supplement), p. 1; retrieved from online Jul. 27, 2011.*
Thomas, R.C., and L.J. Reed, "Disulfide Polymers of DL-α-Lipoic Acid," Journal of the American Chemical Society 78(23):6148-6149, Dec. 1956.
"United States Pharmacopeia—National Formulary (USP 29—NF 24)," United States Pharmacopeial Convention, Rockville, Md., Jan. 2006, USP 29 Physical Tests, Chap. <711> Dissolution, pp. 2675-2682.
Wagner, A.F., et al., "Properties and Derivatives of α-Lipoic Acid," Journal of the American Chemical Society 78(19):5079-5081, Oct. 1956.
Notification of Reasons for Refusal mailed Sep. 20, 2012, issued in corresponding Japanese Application No. 2009-511531, filed Mar. 19, 2009, 7 pages.
Okano, T. (ed.), "Shin-Yakuzaigaku Souron" (New General Pharmaceutics), Nankodo Co., Ltd., 1987, revised 3rd ed., pp. 6-8. (See Notification of Reasons for Refusal of Sep. 20, 2012).

\* cited by examiner

*Primary Examiner* — Bethany Barham
(74) *Attorney, Agent, or Firm* — Christensen O'Connor Johnson Kindness PLLC

(57) ABSTRACT

Lipoic acid pellets are described, obtained from inert cores externally coated with lipoic acid. The so obtained active cores are coated with a first layer of insulating polymeric material and then with a polymeric coat that is insoluble at the gastric pH. Pellet are then formulated pharmaceutically, for instance in jelly capsules or controlled release capsules or as oral suspensions, dispersible powders, sachets, etc.

15 Claims, No Drawings ion is the National Stage of International
LIPOIC ACID PELLETS

CROSS-REFERENCES TO RELATED APPLICATIONS

This applicat Application No. PCT/EP2007/055124, filed May 25, 2007, which claims priority from Italian Application No. MI 2006 A 001024, filed May 25, 2006. Each application is incorporated herein by reference in its entirety.

FIELD OF THE INVENTION

The present invention relates to formulations based on lipoic acid or its analogs.

STATE OF THE ART 1,2-dithiolan-3-pentanoic acid (generally known as lipoic or thioctic acid), is an active principle with antioxidant activity which is used for the treatment of several diseases; moreover, many clinical studies on new therapeutic uses are ongoing in various centers and hospitals. Liver and biliary diseases, polyneuropathies, diabetic polyneuropathies, polyneuropathies associated with other diseases, mushroom poisoning, dementia, viral infections, hypercholesterolemia, dyslipidemia, renal diseases, Alzheimer's disease, tumor pathologies are examples of well-established or experimental therapeutic treatments employing this substance. This compound is interesting also because it promotes metabolism and it is used as support in some pharmacological treatments or therapies, as for instance pharmacological regimens including administration of chemotherapeutic agents, or in patients subjected to cycles of hemodialysis, or in patients undergoing detoxifying treatment.

The preparation of solid dosage forms based on lipoic acid has several problems related to bioavailability, production process, choice of the specific chemical form of the active compound, stability of the compound.

The compound is poorly soluble in water, it has a low melting point, and it is unstable under various environmental conditions, giving rise to polymerization products presumably consisting of linear chains of 6,8-dithiooctanoic acid interconnected by disulphide bonds (B. V. Richard et al., JACS, 78, 1956, 6148-6149; JACS, 78, 1956, 5079-81)

The prior art describes various formulations suitable for oral administration; however said formulations have not yet solved the problems related to this specific active compound.

For instance, pharmaceutical formulations based on lipoic acid have been prepared ensuring plasma levels of lipoic acid for more than 4 hours (EP1082107, Res Medical Institute); these controlled release formulations are tablets or multiple unit dosage forms (e.g. inert cores coated with lipoic acid and an enteric coating agent) obtained by lipoic acid granulation and subsequent addition of methacrylate ester copolymers.

Controlled release tablets containing for instance lipoic acid, characterized by the presence of specific copolymers providing good mechanical resistance during compression, are also known (US20050152977, Roehm). Tablets based on lipoic acid sodium salt have been prepared by direct compression; the so obtained tablets have been then coated with a gastroenteric membrane; these tablets exhibit improved bioavailability compared to tablets containing the active compound in acid form (U.S. Pat. No. 6,348,490, Asta).

SUMMARY OF THE INVENTION

It has now surprisingly been found that lipoic acid formulations can be obtained from inert cores externally coated with lipoic acid. The so obtained active cores are coated with a first layer of insulating polymeric material and then with a polymeric coat that is insoluble at the gastric pH.

DETAILED DESCRIPTION OF THE INVENTION

The term "lipoic acid" used in the present invention comprises the racemic mixture and any other mixture (in different proportions) of R(+) and S(−) enantiomers, as well as the pure forms of individual R(+) and S(−) enantiomers. In addition to the acid form, the above term includes also the salt forms. Lipoic acid salts with carnitine (WO04094403) are also included among salt forms. It is possible to use a commercially available lipoic acid, or lipoic acid can be produced according to processes described for instance in WO02300917, WO02300918, WO02300919, MI2005A00466.

The pellets of the invention are composed of inert cores coated with lipoic acid (herein defined as "active cores") and further coated with two polymeric coats: an internal insulating layer and an outer polymeric membrane that is insoluble at acid pH.

Inert cores can be selected from sucrose cores, microcrystalline cellulose cores or cores made of other inert materials. Cores with defined sizes are commercially available, and can be chosen on the basis of the desired size. For instance, microcrystalline cellulose cores (Cellets) are available with a particle size distribution ranging from 200 to 355 µm (>96%), or from 100 to 200 µm (>96%); such cores have a bulk density of 0.80 g/cm$^3$; are insoluble in water and ethanol and have a spherical grade of 0.90. Sucrose cores are commercially available under the name "sugar spheres"; for instance it is possible to use sugar spheres of size 35 with a granulometry: >425 µm≥90%; >600 µm≤10%; >710 µm=0%, apparent density after settling: 0.8-1.1 g/ml.

Inert cores have the advantage that their size is defined and homogeneous. Consequently, lipoic acid coating results in active cores of homogeneous size, thereby ensuring high reproducibility of the final product. Furthermore, the use of these inert cores makes possible to load high amounts of lipoic acid and therefore to obtain final products containing high amounts of active compound. A further advantage of using inert cores is represented by the fact that it is possible to prepare products based on lipoic acid not involving steps leading to lipoic acid degradation; in fact, the process of preparation of the pellet of the invention requires the application of techniques that allow preservation of the chemical integrity of lipoic acid.

The amount of lipoic acid present on the inert core depends on the type and size of the core, on application purposes as well as on the final dose desired. The amount of lipoic acid applied to the core generally ranges from 5 to 60% of the weight of the active core as defined previously; the optimal amount is determined by the expert in the field.

To the so obtained active core, an insulating layer composed of a polymeric coat is added. The coat comprises one or several polymers, among which hydroxypropyl methylcellulose (HPMC) (Opadry, Pharmacoat) is preferred. Other polymers as for instance hydroxypropylcellulose (HPC), polyvinylalcohol, gum arabic, polyvinylpirrolidone, Kollidon A64 (copolyvidone), polyethylene-glycol can also be used for this purpose. An example of insulating coat is a suspension of HPC (Klucel LF) and talc in ethanol. This coat separates lipoic acid from the external gastroresistant polymeric layer.

At last, a further external polymeric coat is provided, laying externally to the active cores coated with the insulating layer. Said further coat may provide a gastroprotective effect to the pellets; alternatively, it provides a gastroresistant effect. Several kind of polymers may be used to prepare this further coat. Examples thereof are polymers with a pK ensuring their insolubility at low pH values, typically below 5. Representative examples include cellulose esters and their derivatives (like for instance cellulose acetate phthalate, hydroxypropylmethylcellulose phthalate, hydroxypropylmethylcellulose acetate phthalate, hydroxypropylmethylcellulose acetate succinate), polyvinyl acetate-phthalate, copolymers of methacrylic acid and methyl acrylate esters, shellac. These polymers are commercially available with the registered trademarks Cellacefate (cellulose acetate phthalate), Eudragit L100, S100, L30D, aquateric (cellulose acetate phthalate), Aquoat (cellulose acetate phthalate, hydroxypropyl methylcellulose phthalate, hydroxypropyl methylcellulose acetate succinate), HP55 (hydroxypropyl methylcellulose phthalate). Said further external coat can be also formed by a mixture of the above listed polymers or polymers with similar characteristics or mixtures thereof. The selection of the mixture can be performed in order to obtain a release profile suitable for the specific final application desired. The total weight of the polymeric coats (first+second coat) depends on the type of core used, on the amount of lipoic acid loaded, on the desired solubilization profile; it can range from 5 to 60%, preferably from 10 to 60% in weight on total pellet weight; by total pellet weight it is meant the weight of the active core plus the double polymeric coat.

Therefore, this coat represents a homogeneous layer that completely isolates lipoic acid from the external environment.

The second coat can contain a plasticizer selected from: triacetin, tibutyl citrate, triethyl citrate, acetyl tri-n-butyl citrate diethyl phthalate, dibutyl sebacate. The plasticizer can be added in an amount equal to 3-30% in weight of the gastroresistant polymer, preferably 8-25% in weight, even more preferably 10%. The choice and the amount of plasticizer depend on the polymer, on the type of coat selected for film deposition (organic solvent, aqueous solvent, suspension, powders).

The present invention also relates to a process for preparation of the lipoic acid pellet described above, comprising the following steps:
(i) application of lipoic acid on inert cores, yielding active cores
(ii) application of a polymeric insulating-coat on the active cores obtained in step (i)
(iii) application of a polymeric coat on the active cores obtained in step (ii)
(iv) drying and recovery of the coated active cores obtained in step (iii).

Application of the active compound is made in step (i) by adding lipoic acid, in the form of solution, powder or dispersion, to the cores. In case of aqueous suspension, lipoic acid may be suspended in water either in presence or absence of a ligand. The use of a ligand, such as methocel, may improve the performance of the suspension when it is used in the layering step. Instead or together with a ligand, some other ingredients may be added so as to improve the stability of lipoic acid; examples of these ingredients are: ammonium salts, EDTA salts.

In case the application in the solvent form is chosen, for example ethanol, acetone or other solvents or their mixtures thereof can be used. Also other mixtures of organic solvents with buffer solutions can be used, for example mixtures of ethanol and phosphate buffers. These mixtures can be composed by ethanol/phosphate buffer 50 mM pH:6.8 in proportions ranging from 80:20 to 90:10. In these solutions, lipoic acid is stable for at least 24 hours if stored at room temperature and protected from light. Lipoic acid is dissolved in these solvents at an optimal concentration ranging from 20 to 30% w/w, depending on the type of solvent or solvent mixture used. Application of the lipoic acid solution on the core is performed by wetting and subsequent evaporation of the solvent in presence of air at a temperature lower than 40° C., preferably ranging between 36 and 38° C. This procedure yields active cores with a low content of residual solvents.

Step (ii) involves coating active cores with an insulating polymeric film. The coating polymer can be applied starting from solutions or dispersions and is chosen from those previously listed. The solvent selected to disperse the polymer depends on the polymer itself and can be an aqueous or an organic solvent. Solutions or polymeric dispersions commercially available can also be used. This coat can be applied to the core by coating techniques commonly used in the field, as for instance fluid bed coating, basin, etc. At last solvents are removed by techniques that keep the chemical structure of lipoic acid intact.

The polymer is applied in amount that varies depending on the final product desired; also the choice of insulating material depends on the final shape desired.

Step (iii) involves deposition of the polymeric layer on the cores coated with the insulating layer.

For deposition of this polymeric layer, polymer solutions in organic solvents, for instance ethanol, acetone, or aqueous suspensions of the polymer are used. Polymers are chosen from those listed above. The coating technique can be chosen from the techniques commonly used in this field, operating for instance on bed fluid or basin.

In step (iv) pellets are dried according to procedures well known to the expert in the field, enabling removal of residual solvents from the manufacturing process.

During steps (i)-(iii) of the process, drying steps can be introduced in order to remove residual solvents used to obtain intermediate products.

Gastroresistance of the pellets of the invention can be assessed by using the dissolving method of American Pharmacopeia USXXIX, General chapter <711> involving the use of apparatus 1 (basket) or apparatus 2 (paddle). A two step solubilization medium is used: In the first two hours the product is incubated in hydrochloric acid solution, followed by incubation for at least 45 additional minutes in phosphate buffer pH=6.8. The method allows measurement of lipoic acid release at regular intervals.

The present invention also comprises pharmaceutical compositions for oral administration, containing the lipoic acid pellets of the invention mixed with suitable excipients. Due to their special structure, the pellets of the invention make possible to obtain stable products by simple production processes, therefore solving manufacturing problems resulting from the use of lipoic acid mixtures with ingredients different from those used in the pellets of the invention. The pellets of the invention can be indifferently used for preparation of capsules, for instance soft or hard jelly capsules, controlled release capsules, oral suspensions, dispersible powders, sachets or any other pharmaceutical oral form.

Preferred pharmaceutical forms contain 100 mg, 300 mg or 600 mg of lipoic acid per administration form.

In addition, other forms containing higher amounts of lipoic acid, for instance 1 g and 1.5 g, can also be prepared with the pellets of the invention.

Formulations for alimentary use are also object of the present invention. In fact, in the alimentary field, lipoic acid pellets can be used as nutritional additives for specific foodstuff, for instance in foodstuff with acid pH.

Moreover, said pellets can be used for preparation of nutritional supplements. Furthermore, object of the present invention is the use of a pellet as previously described, for preparation of a drug useful for the treatment of pathological conditions responsive to lipoic acid treatment, as well as the use of said pellet as nutritional supplement.

The invention is further illustrated with the following non-limiting examples.

EXPERIMENTAL PART

Example 1

1.A Preparation of Cores Loaded with Lipoic Acid 25% w/w

To prepare a lipoic acid solution in ethanol, 720 g of lipoic acid are poured in 2880 g of ethanol and stirred until a clear solution is obtained, the solution is protected from light and operations are performed with a constant nitrogen flow on the surface. This solution is stored refrigerated.

For application of the lipoic acid solution in ethanol on the cores, a fluid bed Glatt GPCG-1 instrument is used, that is equipped with a 6" si Wurster insert, partitioning tubing with standard diameter and a length of 200 mm which is placed at 15 mm from the bottom, TYPE "B" plate with a metal net of 300 µm (50 mesh), 0.8 mm nozzle. The Glatt GPCC is loaded with 2000 g of sugar spheres of size 35 (granulometry: >425 µm≥90%; >600 µm≤10%; >710 µl m=0%, apparent density after settling: 0.8-1.1 g/ml).

Lipoic acid is applied to sugar spheres by spraying 3334 g lipoic acid solution (20%) in ethanol (80%), using the following process parameters: spraying pressure: 1.5 bar, flow of sprayed solution: about 12 g/min, product temperature during the spraying phase: 34-37° C., flap aperture: 40-50%, fluidification air speed: 3.5-4.5 m/sec (flow 90-115 m³/h). Lipoic acid loaded cores are then dried in fluid bed for 15 minutes at 35° C. The product is discharged and passed through a 840 µm net (about 20 mesh). The residual ethanol present in the pellets is 155 ppm. This process step did not affect the stability of lipoic acid. In fact, the content of lipoic acid after the process step remains the same as the one measured before the treatment (measured by HPLC).

1.B Application of the Insulating Layer

A Klucel LF (3.0%)-Talc<75 µm (1.5%) suspension is prepared in ethanol (95.5%) by adding 90 g of Klucel LF to 2865 g ethanol; the suspension is stirred until a clear solution is obtained. An amount of 45 g talc<75 µm is added and the system is stirred during the whole application phase.

An amount of 2518 g of lipoic acid loaded nuclei is sprayed with 641 g of Klucel LF-Talc suspension in ethanol. The above described Glatt GPCG-1 fluid bed equipment is used for the application. The working parameters are: spraying pressure: 1.5 bar, flow of sprayed suspension: about 10 g/min, product temperature during the spraying phase: 32-34° C., flap aperture: 45-55%, fluidification air speed: 4-5.5 m/sec (flow 100-145 m³/h). The product is then dried for 15 minutes at 35° C., discharged and passed through a 840 µm net (about 20 mesh). The residual ethanol present in the pellets is 123 ppm. In fact, the content of lipoic acid after the process step remains the same as the one measured before the treatment (measured by HPLC).

1.C Application of the Polymeric Gastroresistant Layer

To prepare the suspension: HP55 (7.50%)-Talc<75 µm (3.75%)-Triethyl citrate (0.75%)-Acetone (8.00%) and Ethanol (80.%); 1840 g ethanol and 184 g acetone are weighed in a beaker. An amount of 172.5 g of HP-55 is added and the suspension is stirred until it is completely dissolved. Amounts of 17.25 g of TEC and 86.25 g of talc<75 µm, respectively, are added and the system is stirred during the entire application phase.

An amount of 1,000 g of pellets coated with the insulating layer is sprayed with 2,083 g of HP55-Talc-Triethyl citrate suspension in Acetone and Ethanol. The above described Glatt GPCG-1 fluid bed equipment is used for the application. The working parameters are: spraying pressure: 1.5 bar, flow of sprayed suspension: about 9 g/min, product temperature during the spraying phase: 32-34° C., flap aperture: 45%, fluidification air speed: 3.5-4 m/sec (flow 90-105 m³/h). The product is dried for 25 minutes at 35° C., then is discharged and passed through a 1085 µm net (about 18 mesh).

The pellets are stable: the lipoic acid content remains unvaried after storage for one year both at room temperature and after storage at 4° C. (measured by HPLC). Moreover, also the release profile of the lipoic acid from the pellets stored for one year at room temperature or stored at 4° C. remains substantially the same as that obtained on the fresh preparation (HCl 0.01 N, 2 h; pH: 6.8, phosphate buffer, 37° C.).

Example 2

2.A Preparation of Cores Loaded with Lipoic Acid 25% w/w

The lipoic acid solution in ethanol is prepared as described in the previous example. This solution is stored refrigerated.

For application of the lipoic acid solution in ethanol to the cores, a fluid bed Glatt GPCG-1 instrument is used. The Glatt GPCC is loaded with 2000 g Sugar spheres of size 35. Lipoic acid is applied to the sugar spheres by spraying 3334 g of lipoic acid solution (20%) in ethanol (80%), using the process parameters described in the previous example. Lipoic acid loaded nuclei are then dried in fluid bed for 15 minutes at 35° C. The product is discharged and passed through a 840 µm net.

2.B Application of the Insulating Layer

A Methocel E5 (4.97%)-Avicel PH105 (1.49%) suspension is prepared in ethanol (74.37%)-Acetone (18.59%)-Purified water (0.58%) by addition of 54 g of Methocel E5 to 808.2 g of ethanol; the suspension is stirred until a clear solution is obtained. Acetone 202 g, purified water 6.3 g and, at last, 16.2 g of Avicel PH105 are added and the system is stirred during the entire application phase.

An amount of 1,100 g of lipoic acid loaded nuclei is sprayed with 710 g of Methocel E5-Avicel PH105 suspension in Ethanol-Acetone-Purified water. The above described Glatt GPCG-1 fluid bed equipment is used for the application under the same conditions as above. The product is then dried for 15 minutes at 35° C., discharged and passed through a 840 µm net.

2.C Application of the Polymeric Gastroresistant Layer

To prepare the suspension: HP55 (7.50%)-Talc<75 µm (3.75%)-Triethyl citrate (0.75%)-in Acetone (8.00%) and Ethanol (80.%), 1840 g of ethanol and 184 g of acetone are weighed in a beaker. An amount of 172.5 g of HP-55 is added and the suspension is stirred until it is completely dissolved. 17.25 g of TEC and 86.25 g of talc<75 µm, respectively, are added and the system is stirred during the whole application phase.

An amount of 1,000 g of pellets coated with the insulating layer is sprayed with 2,083 g of HP55-Talc-Triethyl citrate suspension in Acetone and Ethanol. The above described Glatt GPCG-1 fluid bed equipment is used for the application. Working parameters are those described for application of the gastroresistant layer in the previous example. The product is dried for 25 minutes at 35° C., then it is discharged and passed through a 1085 μm net (about 18 mesh).

Example 3

3.A Preparation of Lipoic Acid-Layered Inert Cores

A suspension containing the following ingredients was prepared: lipoic acid (500 g), Methocel E5 (50 g), simethicone (1.1 g), water (1450 g) by stirring at room temperature. Before performing the drug layering this suspension was milled in MI010E.

Fluid Bed 082E equipped with a 1.5 cm Wurster insert, air-distribution plate B, atomization air pressure of 1.7-2 bar, air flow of 2.0-2.5 m/s, was charged with 500 g of Cellets Spheres 350 (350-500 μm>85%, density after settling: 0.8+/−5% g/l).

Drug layering was performed by spraying the above lipoic acid aqueous suspension at a flow rate of 3.4-4.8 g/min while maintaining the product temperature at about 22-28° C. The drug layering was carried out in 355 minutes.

The drug-layered cores were dried in the unit for 30 min at 34-35° C. at air flow of 2.0-2.5 m/sec while maintaining the product temperature at 36° C., to drive off residual water.

The lipoic acid content measured on the drug layered cores is the same as the starting amount of lipoic acid (measured by HPLC), therefore the treatment of drug layering did not affect the stability of lipoic acid.

3.B Application of the Insulating Layer (Methocel E5P/Talc)

The suspension of methocel E5P/talc having the following composition: methocel E5P (12.6 g), talc (1.4 g), water (126 g) was prepared by adding methocel to water, followed by the talc addition immediately prior to the application. The Fluid Bed 082E equipped with a 1.5 cm Wurster insert, air-distribution plate B, atomization air pressure of 1.5-2 bar, air speed of 2.0-2.5 m/s, was charged with the lipoic acid cores prepared in A (700 g).

The layering of this coat was performed by spraying the suspension methocel E5P/talc/water at a flow rate of 3.3 g/min while maintaining the product temperature at about 26-29° C. The layering was carried out in 41 minutes.

3.C Application of the External Polymeric Layer (HP55/Talc/TEC)

The suspension of HP55/Talc/TEC having the following composition: HP55 (14.72 g), NaHCO3 (3.76 g), talc (1.44 g), TEC (1.44 g), water (267.8) was prepared by adding HP 55 and NaHCO3 to water, whereas talc and TEC were added immediately prior to the application. The Fluid Bed 082E equipped with a 1.5 cm Wurster insert, air-distribution plate B, atomization air pressure of 2 bar, air speed of 2.5-3.0 m/s, was charged with the lipoic acid cores layered with the coat (prepared in B).

The layering of this outer layer was performed by spraying the HP55/talc/TEC suspension at a flow rate of 4.9 g/min while maintaining the product temperature at about 26-28° C. The layering was carried out in 60 minutes.

The obtained pellets were then dried for 36 min while maintaining the product temperature at 36° C.

Example 4

4.A Preparation of Lipoic Acid-Layered Inert Cores

A suspension containing the following ingredient was prepared: lipoic acid (800 g), Methocel E5 (80 g), simethicone (few drops), water (1700 g) by stirring at room temperature. Before performing the drug layering this suspension was milled in MI010E.

Fluid Bed 082E equipped with a 1.5 cm Wurster insert, air-distribution plate B, atomization air pressure of 2 bar, air flow of 2.5 m/s, was charged with 500 g of Cellets Spheres 350.

Drug layering was performed by spraying the above lipoic acid aqueous suspension at a flow rate of 2.9-6.7 g/min while maintaining the product temperature at about 24-28° C. The drug layering was carried out in 317 minutes. The drug-layered cores were dried in the unit for 30 min at 34-35° C., at air speed of 2.5 m/sec while maintaining the product temperature at 36° C., to drive off residual water.

No degradation of lipoic acid was detected after the layering step: in fact the original amount of lipoic acid was found in the drug-layered cores (HPLC measurement)

4.B Application of the Insulating Layer (Methocel E5P/Talc)

The suspension of methocel E5P/talc having the following composition: methocel E5P (12.6 g), talc (28 g), water (126 g) was prepared by adding methocel to water, followed by the talc addition immediately prior to the application. The Fluid Bed 082E equipped with a 1.5 cm Wurster insert, air-distribution plate B, atomization air pressure of 2 bar, air speed of 2.5 m/s, was charged with the lipoic acid cores prepared in A (700 g).

The layering of this coat was performed by spraying the suspension methocel E5P/talc/water at a flow rate of 3.4 g/min while maintaining the product temperature at about 31° C. The layering was carried out in 40 minutes.

4.C Application of the External Polymeric Layer (HP55/Talc/TEC)

The suspension of HP55/Talc/TEC having the following composition: HP55 14.72 g, NaHCO3 3.76 g, talc 7.2 g, TEC 1.44 g, water 267.8 g was prepared by adding HP55 and NaHCO3 to water, whereas talc and TEC were added immediately prior to the application. The Fluid Bed 082E equipped with a 1.5 cm Wurster insert, air-distribution plate B, atomization air pressure of 2 bar, air speed of 2.5 m/s, was charged with the lipoic acid cores layered with the coat (prepared in B).

The layering of this outer layer was performed by spraying the HP55/talc/TEC suspension at a flow rate of 3.4 g/min while maintaining the product temperature at about 32-33° C. The layering was carried out in 88 minutes.

The obtained pellets were then dried for 30 min while maintaining the product temperature at 36° C.

These pellets are stable both at 4° C. and at room temperature for at least about five weeks (HPLC measurement).

Example 5

5.A Preparation of Lipoic Acid-Layered Inert Cores

Lipoic acid (500 g) was added to ethanol (1500 g) while stirring at 10° C. Fluid Bed 082E equipped with a 1.5 cm Wurster insert, air-distribution plate B, atomization air pressure of 1.7-2 bar, air flow of 2.0-2.5 m/s, was charged with 500 g of Cellets Spheres 350.

Drug layering was performed by spraying the 25% w/w lipoic acid-ethanol solution at a flow rate of 2.9-8.2 g/min while maintaining the product temperature at about 24-30° C. The drug layering was carried out in 270 minutes.

The drug-layered cores were dried in the unit for 30 min at 34-35° C. at air flow of 2.0-2.5 m/sec while maintaining the product temperature at 36° C., to drive off residual solvent.

The stability of the lipoic acid was not affected by the treatment process, in fact the original amount of lipoic acid has been recovered after the layering step (HPLC measurement).

5.B Application of the Insulating Layer (Methocel E5P/Talc)

The suspension of methocel E5P/talc having the following composition: methocel E5P 12.6 g, talc 2.8 g, water 126 g was prepared by adding methocel to water, followed by the talc addition immediately prior to the application. The Fluid Bed 082E equipped with a 1.5 cm Wurster insert, air-distribution plate B, atomization air pressure of 2 bar, air flow of 2.0 m/s, was charged with the lipoic acid cores prepared in 1.A (700 g).

The layering of this coat was performed by spraying the suspension methocel E5P/talc/water at a flow rate of 3.4 g/min while maintaining the product temperature at about 29-30° C. The layering was carried out in 41 minutes.

5.C Application of the External Polymeric Layer (HP55/Talc/TEC)

The suspension of HP55/Talc/TEC having the following composition: HP55 14.72 g, NaHCO3 3.76 g, talc 7.2 g, TEC 1.44 g, water 26.68 g was prepared by adding HP55 and NaHCO3 to water, whereas talc and TEC were added immediately prior to the application. The Fluid Bed 082E equipped with a 1.5 cm Wurster insert, air-distribution plate B, atomization air pressure of 2 bar, air speed of 2.5-3.0 m/s, was charged with the lipoic acid cores layered with the internal coat (prepared in B).

The layering of this outer layer was performed by spraying the HP55/talc/TEC suspension at a flow rate of 3.4 g/min while maintaining the product temperature at about 30-32° C. The layering was carried out in 87 minutes.

The obtained pellets were then dried for 40 min while maintaining the product temperature at 36° C.

Example 6

6.A Preparation of Lipoic Acid-Layered Inert Cores

α-lipoic acid (500 g) were dissolved in ethanol (2000 g), this solution was maintained protected from light in a thermostated bath (12° C.) and using a nitrogen purge.

The α-lipoic acid solution (2500 g) was then applied onto 2000 g of sugar spheres size 35 (particle size: >425 μm 90%, <600 μm 10%, >710 μm 0%, density after settling: 0.8-1.1 g/ml) using a fluid bed coater (Glatt® GPGC-1) equipped with a 6 inches Wurster insert, partition length 200 mm, partition height locking device 15 mm, orifice plate type B with a screen of 300 μm (50 mesh), nozzle port 0.8 mm. Fluid bed settings were: atomizing air pressure: 1.5 bar, spray rate: about 12 g/min, product temperature: 31-32° C., flap position: 40-50%, inlet air speed: 6.0 m/sec. After drying in the fluid bed for 15 min at 35° C., the coated pellets were sieved through a 840 μm screen (20 mesh).

6.B Application of the Insulating Layer (Pharmacoat)

A water solution of Pharmacoat®606 (hydroxylpropylmethyl cellulose) is prepared. In particular, 40 g of Pharmacoat®606 (8.9% w/w) was added to 401 g of hot water (80° C.). The polymer dispersion was then cooled to room temperature to obtain a limpid solution. Finally, 9 g of talc (2.0% w/w) was added and the system is maintained under stirring during the coating process.

The coating process was carried out in the same apparatus described above. In particular, 400 g of Pharmacoat®606 solution were applied onto 860 g of pellets previously coated with α-lipoic acid. Fluid bed settings are: nozzle port 1.0 mm, atomizing air pressure: 1.5 bar, flow rate: about 4 g/min, product temperature: 33-35° C., flap position: 40%, inlet air speed: 6.0 m/sec.

After drying in fluid bed for 15 min at 35° C., the coated pellets were sieved through a 840 μm screen (20 mesh).

6.C Application of the External Polymeric Layer

An AQOAT®AS-LF (hydroxypropyl cellulose acetate succinate) dispersion was prepared. In particular, 7.35 g of triethylcitrate (0.98% w/w) and 7.89 g of sodium lauryl sulfate (1.05% w/w) were dissolved under stirring in 603.51 g of water first. After complete dissolution of triethylcitrate, 52.50 g of AQOAT®LF (7.01% w/w) and 78.75 g of talc (10.50% w/w) were added gradually while maintaining the system stirred.

The coating process was carried out in fluid bed coater (Glatt® GPGC-1) equipped with a 4 inches Wurster insert, partition length 150 mm, partition height locking device 15 mm, orifice plate type B with a screen of 300 μm (50 mesh), nozzle port 1.0 mm.

The AQOAT®LF dispersion (750 g) was applied onto pellets (650 g) formerly coated with α-lipoic acid and Pharmacoat®606. Fluid bed settings were: atomizing air pressure: 1.5 bar, spray rate: about 3.4 g/min, product temperature during the coating phase: 25-28° C., flap position: 25-30%, inlet air speed: 2.0 m/sec.

After drying in fluid bed for 30 min at 35° C., the coated pellets were sieved through a 840 μm screen (20 mesh).

The invention claimed is:

1. Lipoic acid pellet, comprising an inert core coated with lipoic acid (active core) in an amount from 5 to 60 wt % of the active core, and further coated with a first insulating polymeric coat and with a second external gastroresistant polymeric coat, wherein the total weight of the insulating polymeric coat and the gastroresistant polymeric coat ranges from 5 to 60 wt % of the weight of the total pellet weight.

2. Pellet according to claim 1, wherein the inert core comprises sucrose, microcrystalline cellulose cores or other inert materials.

3. Pellet according to claim 1, wherein lipoic acid is R(+) lipoic acid, S(−) lipoic acid, a salt or a mixture thereof.

4. Pellet according to claim 1, wherein the first insulating polymeric coat comprises hydroxypropylmethylcellulose or hydroxypropylcellulose.

5. Pellet according to claim 1, wherein the second gastroresistant polymeric coat comprises one or more cellulose esters, polyvinyl acetate-phthalate, copolymers of methacrylic acid and methyl acrylate esters, and shellac.

6. Pellet according to claim 5, wherein the second gastroresistant polymeric coat comprises one or more among cellulose acetate phthalate, hydroxypropylmethylcellulose phthalate, hydroxypropylmethylcellulose acetate phthalate, hydroxypropyl methylcellulose acetate succinate, polyvinyl acetate phthalate, poly(methacrylic acid-co-methyl methacrylate) (1:1), poly(methacrylic acid-co-methyl methacrylate) (1:2), and poly(methacrylic acid-co-ethyl acrylate) (1:1).

7. Process for preparation of a lipoic acid pellet according to claim 1, comprising the following steps:
  (i) application of lipoic acid on inert cores to provide active cores;
  (ii) application of a polymeric insulating coat on the active cores obtained in step (i);
  (iii) application of a gastroresistant polymeric coat on the active cores obtained in step (ii);
  (iv) drying and recovery of the coated active cores obtained in step (iii).

8. Pharmaceutical composition for oral administration, comprising the pellet of claim 1, mixed with excipients suitable for pharmaceutical use.

9. Composition according to claim 8, formulated in soft or hard jelly capsules, controlled release capsules, oral suspension, dispersible powder, or sachets.

10. Composition according to claim 8, comprising amounts of lipoic acid ranging from 50 mg to 2 g per administration unit.

11. Nutritional supplement comprising a composition of claim 8.

12. A nutritional supplement comprising the pellet according to claim 1.

13. An additive for foodstuff comprising the pellet according to claim 1.

14. The additive according to claim 13, wherein the foodstuff has an acid pH.

15. A method for the treatment of pathological conditions responsive to lipoic acid treatment, comprising administering to a subject in need thereof an effective amount of lipoic acid pellet according to claim 1.

* * * * *